US011383023B2

(12) United States Patent
Dembo et al.

(10) Patent No.: US 11,383,023 B2
(45) Date of Patent: Jul. 12, 2022

(54) INJECTION PROTOCOL GENERATION DEVICE, INJECTION APPARATUS AND IMAGING SYSTEM INCLUDING GENERATION DEVICE, INJECTION PROTOCOL GENERATION METHOD AND INJECTION PROTOCOL GENERATION PROGRAM

(71) Applicant: NEMOTO KYORINDO CO., LTD., Tokyo (JP)

(72) Inventors: Masayuki Dembo, Tokyo (JP); Kazumasa Masuda, Tokyo (JP); Shigeru Nemoto, Tokyo (JP)

(73) Assignee: NEMOTO KYORINDO CO., LTD., Tokyo (JP)

( * ) Notice: Subject to any disclaimer, the term of this patent is extended or adjusted under 35 U.S.C. 154(b) by 1091 days.

(21) Appl. No.: 15/815,383

(22) Filed: Nov. 16, 2017

(65) Prior Publication Data

US 2018/0133392 A1 May 17, 2018

(30) Foreign Application Priority Data

Nov. 17, 2016 (JP) .............................. JP2016-224084

(51) Int. Cl.
*A61M 5/00* (2006.01)
*A61B 6/03* (2006.01)
*A61B 6/00* (2006.01)

(52) U.S. Cl.
CPC .............. *A61M 5/007* (2013.01); *A61B 6/035* (2013.01); *A61B 6/481* (2013.01);
(Continued)

(58) Field of Classification Search
CPC .......... A61M 5/007; A61M 2205/3334; A61M 2205/3379; A61M 205/3379;
(Continued)

(56) References Cited

U.S. PATENT DOCUMENTS

| 6,397,098 B1 * | 5/2002 | Uber, III | G06F 19/3468 |
| | | | 600/431 |
| 2004/0064040 A1 * | 4/2004 | Masuda | A61M 5/007 |
| | | | 600/431 |

(Continued)

FOREIGN PATENT DOCUMENTS

WO 2016/021185 A1 2/2016

OTHER PUBLICATIONS

Fleischmann, D. et al. "Mathematical Analysis of Arterial Enhancement and Optimization of Bolus Geometry for CT Angiography Using the Discrete Fourier Transform". Journal of Computer Assisted Tomography: May 1999—vol. 23—Issue 3—p. 474-484 (Year: 1999).*

*Primary Examiner* — Boniface Ngathi N
*Assistant Examiner* — Milton Truong
(74) *Attorney, Agent, or Firm* — Studebaker & Brackett PC (57) ABSTRACT

When imaging an imaging subject, a pixel value is maintained in a state of small fluctuation of the pixel value over an entire expected duration. A generation device includes: an imaging information acquiring unit acquiring information of an imaging site of an imaging subject; a subject information acquiring unit acquiring information of the imaging subject; and a protocol generation unit generating an injection protocol for a contrast medium based on the information of the imaging site and the information of the imaging subject, wherein the protocol generation unit generates the injection protocol including a first phase in which an injection rate decreases with a first acceleration, and a second phase which follows the first phase and in which the injection rate decreases with a second acceleration, and the injection rate at a start of the second phase is higher than the injection rate at an end of the first phase.

9 Claims, 6 Drawing Sheets

(52) U.S. Cl.
CPC ............ *A61M 2205/3306* (2013.01); *A61M 2205/3334* (2013.01); *A61M 2205/3379* (2013.01); *A61M 2205/50* (2013.01); *A61M 2205/505* (2013.01); *A61M 2205/52* (2013.01)

(58) Field of Classification Search
CPC ...... A61M 5/1408; A61M 2005/14208; A61B 6/481; G16H 20/17
See application file for complete search history.

(56) References Cited

U.S. PATENT DOCUMENTS

| | | | |
|---|---|---|---|
| 2009/0240142 A1* | 9/2009 | Lawaczek | A61K 49/0438 600/431 |
| 2011/0060219 A1* | 3/2011 | Small | A61M 5/14546 600/432 |
| 2015/0324979 A1* | 11/2015 | Xue | G06T 11/006 382/131 |
| 2016/0278725 A1* | 9/2016 | Van Nijnatten | A61B 6/461 |

* cited by examiner

INJECTION PROTOCOL GENERATION DEVICE, INJECTION APPARATUS AND IMAGING SYSTEM INCLUDING GENERATION DEVICE, INJECTION PROTOCOL GENERATION METHOD AND INJECTION PROTOCOL GENERATION PROGRAM

BACKGROUND OF THE INVENTION

Field of the Invention

The present invention relates to a generation device for an injection protocol of a contrast medium, an injection apparatus and an imaging system including the generation device, an injection protocol generation method, and an injection protocol generation program.

Description of the Related Art

In recent years, medical imaging apparatuses capable of imaging large areas (for example, a region of 16 cm in the craniocaudal direction of an imaging subject) have appeared. An example of such an imaging apparatus is "AquilionONE (registered trademark)" manufactured by Toshiba Medical Systems Corporation. Thus, it is desired to maintain pixel values in a predetermined range over predetermined duration in a large imaging site of an imaging subject.

For example, when an image of a coronary artery of an imaging subject is captured, there is a demand for maintaining a desired pixel value for 10 seconds. Also, since the pixel value of a calcified portion of the coronary artery is about 500 HU, there is a desire for maintaining the pixel value within a predetermined range from 400 HU, for example, so that the pixel value of the coronary artery does not reach 500 HU.

In this respect, WO 2016/021185 A discloses an injection apparatus including a generation device for generating an injection protocol maintaining a predetermined range of a pixel value over predetermined duration, an input unit for inputting at least one of a pixel value and duration, and an injection head for injecting a contrast, medium according to the generated injection protocol.

SUMMARY OF THE INVENTION

By the injection protocol described in WO 2016/021185 A, the pixel value may fluctuate in the latter half of the expected duration. Even in this case, the pixel value within the predetermined range can be maintained. However, it is desirable to maintain the pixel value in a state where the fluctuation of the pixel value is small over the expected duration.

In order to solve the above issue, a generation device as an example of the present invention includes: an imaging information acquiring unit acquiring information of an imaging site of an imaging subject; a subject information acquiring unit acquiring information of the imaging subject; and a protocol generation unit generating an injection protocol for a contrast medium based on the information of the imaging site and the information of the imaging subject, wherein the protocol generation unit generates the injection protocol including a first phase in which an injection rate decreases with a first acceleration, and a second phase which follows the first phase and in which the injection rate decreases with a second acceleration, and the injection rate at a start of the second phase is higher than the injection rate at an end of the first phase.

An injection apparatus as another example of the present invention is an injection apparatus injecting a contrast medium, the injection apparatus includes: the above-described generation device; and an injection head for injecting the contrast medium according to an injection protocol.

An imaging system as another example of the present invention includes: an imaging apparatus imaging an image of an imaging subject; and the above-described generation device.

An injection protocol generation method as another example of the present invention includes: acquiring information of an imaging site of an imaging subject and information of the imaging subject; and generating, based on the information of the imaging site and the information of the imaging subject, the injection protocol including a first phase in which an injection rate decreases with a first acceleration and a second phase which follows the first phase and in which the injection rate decreases with a second acceleration, the injection rate at a start of the second phase being higher than the injection rate at an end of the first phase.

In addition, an injection protocol generation program for a contrast medium as further another example of the present invention causes a generation device for generating an injection protocol to function as: an imaging information acquiring unit acquiring information of an imaging site; a subject information acquiring unit acquiring information of an imaging subject; and a protocol generation unit generating, based on the information of the imaging site and the information of the imaging subject, the injection protocol including a first phase in which an injection rate decreases with a first acceleration, and a second phase which follows the first phase and in which the injection rate decreases with a second acceleration, the injection rate at a start of the second phase being higher than the injection rate at an end of the first phase.

This makes it possible to maintain the pixel value in a state where fluctuation of the pixel value is small over expected entire duration when imaging the imaging subject.

Further features of the present invention will become apparent from the following description of the embodiments illustrated by way of examples with reference to the accompanying drawings.

DESCRIPTION OF THE EMBODIMENTS

Hereinbelow, exemplary embodiments for carrying out the present invention will be described in detail with reference to the drawings. However, the dimensions, materials, shapes and relative positions of the components described in the following embodiments are freely determined and can be changed according to the configuration of an apparatus to which the present invention is applied or to various conditions. Also, unless otherwise specified, the scope of the present invention is not limited to the embodiments specifically described below. Incidentally, unless otherwise mentioned, the term contrast medium includes both a contrast medium alone and a chemical liquid containing other solvents and additives in addition to the contrast medium.

Figure 1:
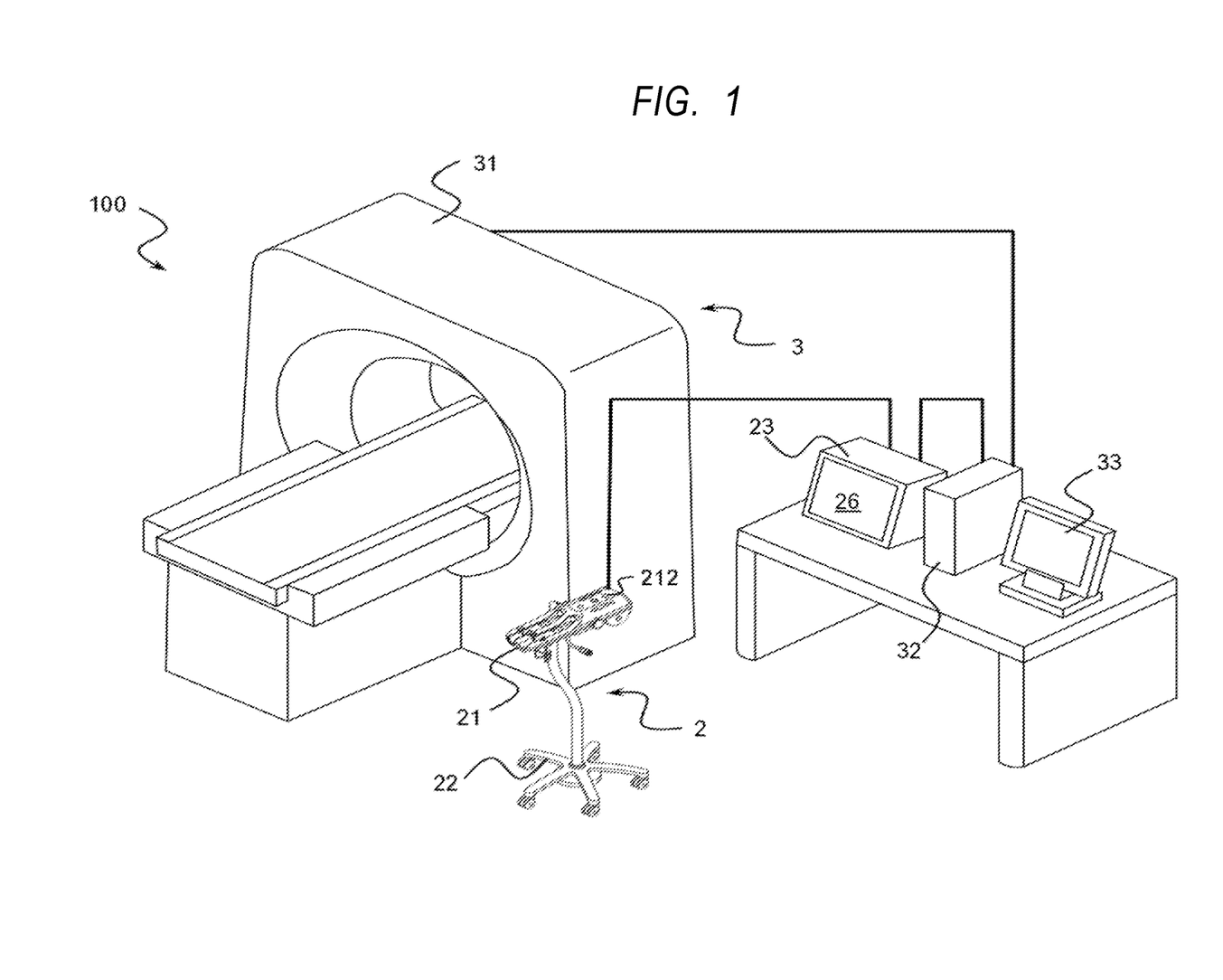
FIG. 1 is a schematic diagram of an imaging system.

As shown in FIG. 1, an imaging system 100 includes an injection apparatus 2 for injecting a contrast medium and an imaging apparatus 3 connected to the injection apparatus 2 in a wired or wireless manner and imaging an imaging subject. The imaging apparatus 3 includes various medical imaging apparatuses such as a magnetic resonance imaging (MRI) apparatus, a computed tomography (CT) apparatus, an angiography imaging apparatus, a positron emission tomography (PET) apparatus, a single photon emission computed tomography (SPECT) apparatus, a CT angiography apparatus, an MR angiography apparatus, an ultrasonic diagnostic apparatus, and a blood vessel imaging apparatus. The CT apparatus will be described below.

The imaging apparatus 3 includes an imaging unit 31 that performs imaging of a test subject, according to the imaging plan and a controller 32 that controls the entire imaging apparatus 3. The imaging plan includes information on an imaging site, an effective tube voltage, a model name, a manufacturer name, imaging time, a tube voltage, an imaging range, a rotation speed, a helical pitch, exposure time, a dose, an imaging method, and the like. Then, the controller 32 controls the imaging unit 31 to capture an image of the test subject so as to follow the imaging plan. Further, the controller 32 can communicate with the imaging unit 31, the injection apparatus 2, and a server (external storage device) by wired or wireless connection.

The imaging unit 31 includes a bed, an X-ray source that irradiates a test subject as an imaging subject with X-rays, an X-ray detector that detects X-rays that have passed through the test subject, and the like. The imaging unit 31 irradiates a test subject with X-rays and captures a fluoroscopic image of the test subject by back projecting the inside of the test subject's body based on the X-rays transmitted, through the test subject. Alternatively, the imaging unit 31 may capture images using radio waves or ultrasonic waves.

Further, the imaging apparatus 3 has a display 33 as a display unit. The display 33 is connected to the controller 32, and displays an input state and a setting state of the apparatus, an imaging result, various information, etc. Alternatively, the controller 32 and the display 33 may be integrally constructed. Further, the imaging apparatus 3 has a user interface such as a keyboard as an input unit (not shown). The operator can input chemical liquid information, imaging information, subject information and/or imaging conditions from the input unit to the imaging apparatus 3.

In the injection apparatus 2, a chemical liquid filled in a syringe, such as physiological saline and various contrast media is injected into the body of a test subject as an imaging subject. This injection protocol includes at least an injection rate and injection time but may further include information on injection conditions such as acceleration of the injection rate, injection volume, injection timing, and a contrast medium concentration and injection pressure. The injection apparatus 2 also includes an injection head 21 for injecting a contrast medium according to an injection protocol. Then, the syringe filled with a chemical liquid is mounted on the injection head 21. The injection apparatus 2 also includes a stand 22 for holding the injection head 21 and a console 23 connected to the injection head 21 in a wired or wireless manner.

The console 23 functions as a controller for controlling the injection head 21 and also functions as a generation device for generating a contrast medium injection protocol. The console 23 has a touch panel 26 functioning as an input/display unit, and can communicate with the injection head 21 and the imaging apparatus 3 by wired or wireless communication. The touch panel 26 displays an injection protocol, an input state and a setting state of the apparatus, an injection result, various information, and the like. Alternatively, the injection apparatus 2 may have a display as a display unit and a user interface such as a keyboard as an input unit.

Instead of the console 23, the injection apparatus 2 may have a controller connected to the injection head 21 and a display unit (for example, a touch panel display) connected to the controller and displaying the injection state of the chemical liquid or the like. Such a controller also functions as an injection protocol generation device. Further, the injection head 21 and the controller can be integrated with the stand 22. Still further, a suspension member may be provided instead of the stand 22, and the injection head 21 may be suspended from the ceiling via the suspension member.

In addition, the injection apparatus 2 may have a power supply or a battery and a remote operation apparatus (e.g., a hand switch) for remotely operating the injection head 21. This remote operation apparatus can start or stop injection by remotely operating the injection head 21. Also, the power supply or the battery can be provided in either the injection head 21 or the controller, or can be provided separately from these devices.

The injection head 21 has a syringe holding portion on which a syringe is mounted, and incorporates a drive mechanism for pushing out the chemical liquid inside the syringe according to the injection protocol. Further, the injection head 21 has an operation section 212 for inputting the operation of the drive mechanism. The operation section 212 is provided with a forward movement button of the drive mechanism, a backward movement button of the drive mechanism, a final confirmation button, and the like. Furthermore, the injection head 21 may be provided with a head display for displaying an injection condition, an injection state, an input state and a setting state of the apparatus, various injection results, etc.

When a contrast medium is injected, an extension tube or the like is connected to the end of the syringe mounted on the injection head 21. When preparation for injection is completed, the operator presses the final confirmation button of the operation section 212. As a result, the injection head 21 stands by in a state where injection can be started. When the injection is started, the contrast medium pushed out of the syringe is injected into the body of the test subject via the extension tube or the like.

Further, various types of syringes such as a prefiiled syringe having a data carrier such as an RFID chip, an IC tag, or a barcode can be mounted on the injection head 21. In addition, the injection head 21 has a reading unit 213 (FIG. 2) therein for reading from a data carrier attached to the syringe. In this data carrier, information related to the chemical liquid (chemical liquid information) is stored. The chemical liquid information includes a product ID, a product name, a chemical classification, an ingredient, a concentration, viscosity, an expiration date, a syringe capacity, syringe pressure resistance, a cylinder inner diameter, a piston stroke, a lot number, and the like.

The injection apparatus 2 can receive information from a server (external storage device) which is not shown and can also transmit information to the server. Also, the imaging apparatus 3 can receive information from the server and can also transmit information to the server. Examples of such servers include a radiology information system (RIS), picture archiving and communication system (PACS), hospital information system (HIS), and the like.

In this server, an examination order is stored in advance. This examination order includes information on the test subject (subject information) and examination information on examination contents. The subject information includes information on body weight, lean body mass, circulating blood volume, a test subject number (test subject ID), a name, sex, a date of birth, age, height, blood volume, body surface area, disease, a heart rate, cardiac output of the imaging subject and the like. In addition, the examination information includes information on an examination number (examination ID), an examination site, an examination date and time, a chemical liquid type, a chemical liquid name, imaging information (information on the imaging site), and the like. Further, the server can store information on the imaging result such as the data of the image transmitted from the imaging apparatus 3 and information on the injection result transmitted from the injection apparatus 2. In order to operate the injection apparatus 2 and the imaging apparatus 3, an external image inspection system or a workstation for creating an image can also be used.

First Embodiment

Figure 2:
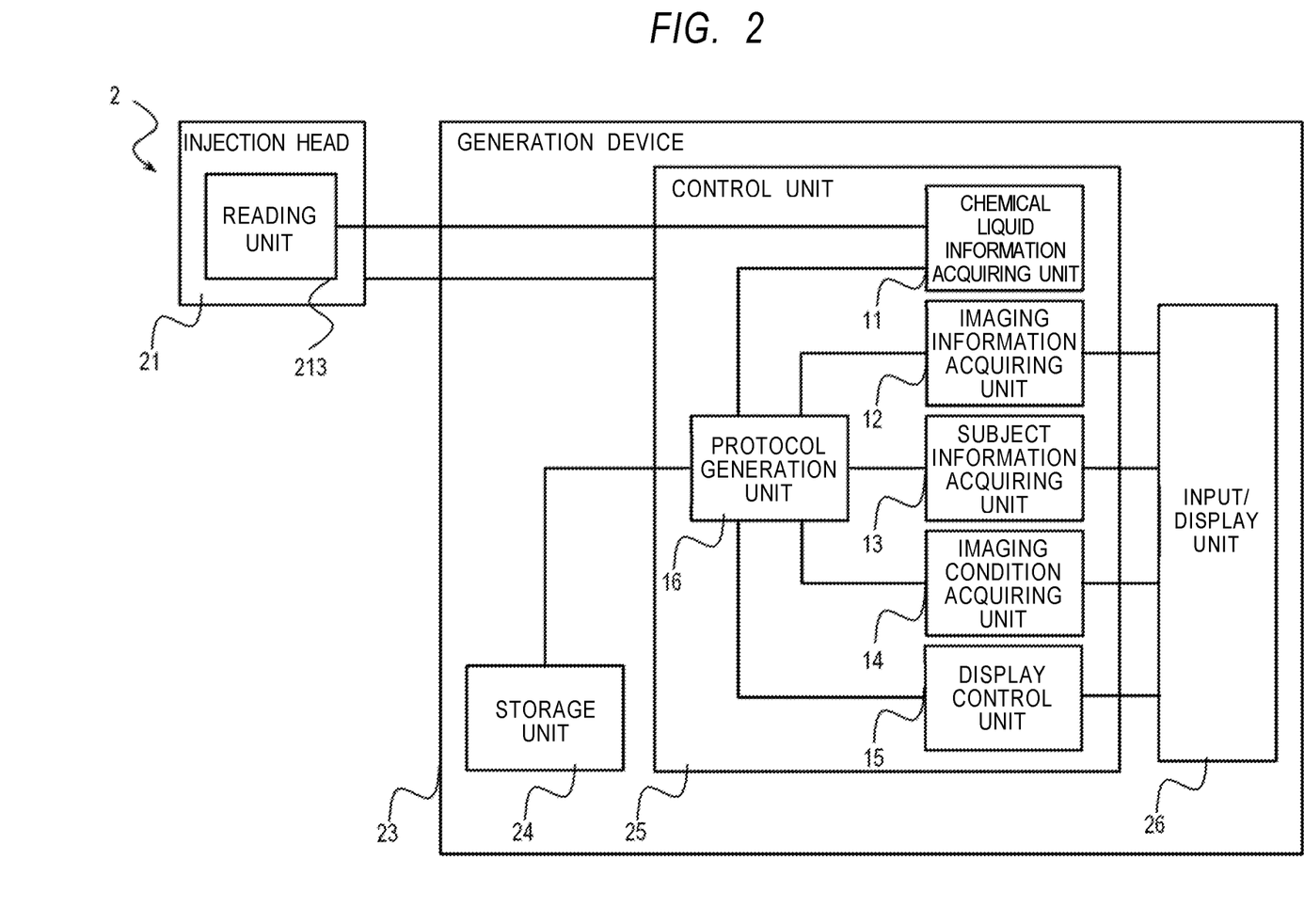
FIG. 2 is a schematic block diagram of an injection apparatus according to a first embodiment of the present invention.
Figure 3:
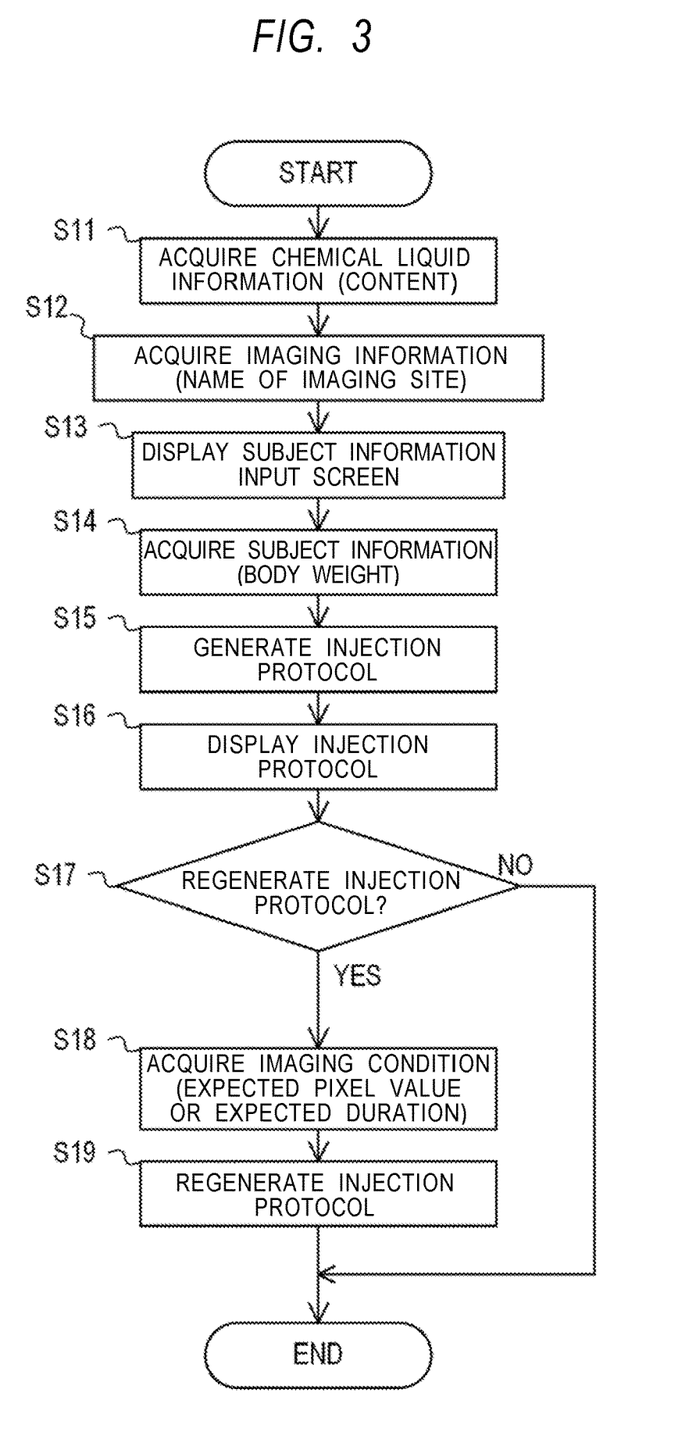
FIG. 3 is a flowchart for illustrating a generation method of an injection protocol.

Next, with reference to FIGS. 2 and 3, an injection protocol generation method will be described. FIG. 2 is a schematic block diagram of the injection apparatus 2, and FIG. 3 is a flowchart illustrating generation of the injection protocol.

As shown in FIG. 2, the console 23 of the injection apparatus 2 has a storage unit 24 that stores a control program, information on an injection protocol, information on chemical liquids, and the like. Further, the console 23 has a control unit 25 such as a CPU that controls the entire injection apparatus 2 including the injection head 21, and the touch panel 26 as an input/display unit. An operator can input a predetermined command, information or the like via the touch panel 26 as an input unit.

The storage unit 24 includes a random access memory (RAM) that is a system work memory for the control unit 25 to operate, a read only memory (ROM) that stores programs or system software, a hard disk drive or the like. The control unit 25 executes various processing corresponding to the program installed in the storage unit 24, whereby each unit is logically operated as various functions. Alternatively, the control unit 25 can also control various processing in accordance with a program stored in a portable recording medium such as a compact disc (CD) and a digital versatile disc (DVD), or an external storage medium such as a server on the Internet.

The control unit 25 includes a chemical liquid information acquiring unit 11 that acquires information on the chemical liquid, an imaging information acquiring unit 12 that acquires information on the imaging site of the imaging subject (imaging information), a subject information acquiring unit 13 that acquires information on an imaging subject (subject information), an imaging condition acquiring unit 14 that acquires at least one of an expected pixel value and expected duration as imaging conditions, a display control unit 15 for controlling the touch panel 26 as a display unit and a protocol generation unit 16 for generating an injection protocol of a contrast medium based on the information on the imaging site and the information on the imaging subject.

The information on the imaging site is information that can specify the imaging site (range), such as the name of the imaging method, the distance from the injection site to the imaging site. Further, the expected pixel value is a desired pixel value required for imaging of the imaging site, and can be set in advance for each imaging site or can be input from the input unit by the operator. The expected duration is desired time for maintaining the expected pixel value, which can be preset for each imaging site or can be input by the operator from the input unit.

The injection protocol generation program of the contrast medium installed in the storage unit 24 causes a generation device 23 as a computer for generating an injection protocol to function as the imaging information acquiring unit 12 for acquiring information on the imaging site, the subject information acquiring unit 13 for acquiring information on the imaging subject, and the protocol generation unit 16 that generates an injection protocol based on the information on the imaging site and the information on the imaging subject. At this time, the protocol generation unit 16 generates an injection protocol so that the injection protocol includes a first phase in which the injection rate decreases with the first acceleration, a second phase which follows the first phase and in which the injection rate decreases with the second acceleration, and in addition, the injection rate at the beginning of the second phase is higher than the injection rate at the end of the first phase. The injection protocol generation program is stored in a computer readable recording medium.

The operator places a syringe in the injection head 21 after turning on the power supply of the injection apparatus 2. Then, as shown in FIG. 3, the reading unit 213 of the injection head 21 reads chemical liquid information (for example, product ID and iodine content) and sends the information to the chemical liquid information acquiring unit 11. Then, the chemical liquid information acquiring unit 11 acquires the chemical liquid information read by the reading unit 213 (S11). Alternatively, the chemical liquid information acquiring unit 11 can acquire chemical liquid information also from the imaging apparatus 3 or an external server. Further, the chemical liquid information acquiring unit 11 can acquire chemical liquid information inputted by the operator via the touch panel 26 as an input unit.

Then, the protocol generation unit 16 causes the storage unit 24 to store temporarily the chemical liquid information acquired by the chemical liquid information acquiring unit 11. At the same time, the display control unit 15 causes the touch panel 26 to display the product name and the iodine content based on the chemical liquid information received from the protocol generation unit 16. At this time, the display control unit 15 causes the touch panel 26 as a display unit to display also an input screen for imaging information.

Next, the operator selects a desired imaging site (for example, an aorta) from the plurality of sites displayed on the touch panel 26. Then, the imaging information acquiring unit 12 acquires imaging information (for example, the name of the imaging site) via the touch panel 26 as an input unit (S12). Then, the protocol generation unit 16 causes the storage unit 24 to store temporarily the imaging information acquired by the imaging information acquiring unit 12. Alternatively, the imaging information acquiring unit 12 can also acquire imaging information from the imaging apparatus 3 or an external server. Thereafter, the display control unit 15 causes the touch panel 26 as the display unit to display an input screen for the subject information (S13).

The operator inputs subject information (for example, a numerical value of 60 kg as the body weight of the imaging subject) via the touch panel 26. Then, the subject information acquiring unit 13 acquires the imaging subject's body weight as the subject information via the touch panel 26 as the input unit (S14). Alternatively, the subject information acquiring unit 13 can acquire subject information from the imaging apparatus 3, an external server or an external measuring device (for example, a weight scale). The protocol generation unit 16 causes the storage unit 24 to store temporarily the subject information acquired by the subject information acquiring unit 13. At the same time, the display control unit 15 causes the touch panel 26 as the display unit to display the subject information.

The order of acquisition of the chemical liquid information, imaging information, subject information, and imaging condition can be appropriately changed. For example, after obtaining the name of the imaging site as the imaging information, the content of the contrast medium alone in the chemical liquid may be acquired as the chemical liquid information. Further, the chemical liquid information, the imaging information and the subject information can be stored in the storage unit 24 before the examination. In this case, the chemical liquid information acquiring unit 11, the imaging information acquiring unit 12, and the subject information acquiring unit 13 can also acquire the respective information from the storage unit 24. For example, when the chemical liquid information acquiring unit 11 does not acquire chemical liquid information from the reading unit 213, the unit acquires predetermined chemical liquid information from the storage unit 24.

Then, based on the imaging information and the subject information, the protocol generation unit 16 generates the injection protocol of the contrast medium by calculation (S15). To be specific, the usage volume per unit time of the contrast medium alone per body weight (for example, the amount of iodine to be used per body weight), the injection time, and the acceleration of the injection rate (change rate of the injection volume per unit time) are stored in the storage unit 24 in advance. Then, the protocol generation unit 16 reads the usage volume per body weight, the injection time and the acceleration associated with the imaging information from the storage unit 24. Furthermore, the protocol generation unit 16 reads the content as the chemical liquid information from the storage unit 24.

Further, the usage amount per unit time of the contrast medium alone per body weight and the injection time associated with the name of the imaging method may be stored in the storage unit 24 in advance. In this case, the protocol generation unit 16 reads the usage amount per body weight and the injection time associated with the name of the imaging method from the storage unit 24.

When generating the injection protocol, the protocol generation unit 16 calculates the injection rate at the start of the first phase. At this time, a predetermined multiplication factor K constituted by a value greater than 1 is used so that the injection rate at the start of the second phase is lower than the injection rate at the start of the first phase. In the first embodiment, the multiplication factor K=1.1 is set as a range that does not largely affect the total injection volume of the contrast medium. Then, assuming that the usage amount per body weight is UIO (mgI/Kg/sec), the body weight of the test subject is W (kg), and the content of the contrast medium alone is CM (mgI/mL), the injection rate $SV_1$ (mL/sec) at the beginning of the first phase is obtained by the following Formula 1.

$$SV_1 = UIO \times W/CM \times K \quad \text{(Formula 1)}$$

For example, when the imaging site is an aorta, the usage amount per body weight of the first phase is 35.5 mgI/Kg/sec. Assuming that the content is 300 mgI/mL and the body weight of the test subject is 40 kg, when each value is substituted into Formula 1, an injection rate of 5.2 mL/sec at the start of the first phase is obtained. Incidentally, the multiplication factor K need not be used unless it is necessary, and the multiplication factor K=1 may be set.

Subsequently, the protocol generation unit 16 calculates the injection rate at the start of the second phase. Assuming that the usage amount per body weight is UIO (mgI/Kg/sec), the body weight of the test subject is W (kg), and the content of the contrast medium alone is CM (mgI/mL), the injection rate $SV_2$ at the start of the second phase (mL/sec) is obtained by the following Formula 2.

$$SV_2 = UIO \times W/CM \quad \text{(Formula 2)}$$

For example, when the imaging site is an aorta, the usage amount per body weight in the second phase is 19.5 mgI/Kg/sec. Assuming that the content is 300 mgI/mL and the body weight of the test subject is 40 kg, when each value is substituted into Formula 2, an injection rate of 2.6 mL/sec at the start of the second phase is obtained.

Next, the protocol generation unit 16 calculates the injection rate $EV_0$ at the ends of the first phase and the second phase using the injection rate $SV_1$ at the start of the first phase, the injection rate $SV_2$ at the start of the second phase, the injection time $T_0$ (sec) of each phase and the acceleration $D_0$ (mL/s$^2$) of each phase read out from the storage unit 24. Here, the acceleration $D_0$ in each phase is set so that the injection rate decreases with the first acceleration in the first phase and the injection rate decreases with the second acceleration in the second phase following the first phase. Further, the acceleration $D_0$ in each phase is set so that the injection rate at the start of the second phase is higher than the injection rate at the end of the first phase.

Further, the acceleration $D_0$ can be set so that the injection rate linearly decreases in the first phase or the second phase. Further, the acceleration $D_0$ can be set so that the second acceleration in the second phase is greater than the first acceleration in the first phase. In addition, the acceleration $D_0$ can be set so that the change amount of the injection rate in the second phase is smaller than the change amount of the injection rate in the first phase. Further, the acceleration $D_0$ can be set so that the injection volume in the second phase is smaller than the injection volume in the first phase. The injection rate $EV_0$ at the end of each phase is obtained by the following Formula 2 using the injection time $T_0$ and the acceleration $D_0$.

$$EV_0 = SV_0 + (D_0 \times T_0) \quad \text{(Formula 3)}$$

For example, when the imaging site is an aorta, the injection time $T_1$ of the first phase is 7.27 seconds and the negative acceleration $D_1$ of the first phase is −0.371 mL/s$^2$. When these values are substituted into Formula 3, the injection rate $EV_1$ at the end of the first phase is 2.5 mL/sec. Similarly, the injection time $T_2$ in the second phase is 8 seconds and the negative acceleration $D_2$ in the second phase is −0.025 mL/s$^2$. When these values are substituted into Formula 3, the injection rate $EV_2$ at the end of the second phase is 2.4 mL/sec.

The protocol generation unit 16 calculates the total injection volume $SUM_0$ of the contrast medium in the first phase and the second phase by using the injection rate $SV_1$ at the start of the first phase, the injection rate $SV_2$ at the start of the second phase, the injection time $T_0$ (sec) of each phase and the acceleration $D_0$ (mL/s$^2$) of each phase read out from the storage unit 24. The injection time $T_0$ can be set so that the injection time in the second phase is longer than the injection time in the first phase. The total injection volume $SUM_0$ (mL) of each phase is obtained by the following Formula 4.

$$SUM_0 = (SV_0 + EV_0) \times T_0 / 2 \quad \text{(Formula 4)}$$

For example, when the injection rate 5.2 mL/sec at the start of the first phase, the injection rate 2.5 mL/sec at the end of the first phase, and the injection time 7.27 seconds of the first phase are substituted into Formula 4, the total injection volume $SUM_1$ for the first phase is 28 mL. Similarly, when the injection rate 2.6 mL/sec at the start of the second phase, the injection rate 2.4 mL/sec at the end of the second phase, and the injection time 8 seconds of the second phase are substituted into Formula 4, the total injection volume $SUM_2$ of the second phase is 20 mL.

MODIFICATION EXAMPLE

As described above, the protocol generation unit 16 generates an injection protocol including an injection rate and injection time. Alternatively, the protocol generation unit 16 may read out the injection protocol corresponding to information on the imaging site and information on the imaging subject from the storage unit 24, thereby generating the injection protocol. In this case, the storage unit 24 stores an injection protocol that includes a first phase in which the injection rate decreases with the first acceleration and a second phase which follows the first phase and in which the injection rate decreases with the second acceleration such that the injection rate at the beginning of the second phase is higher than the injection rate at the end of the first phase. For example, the storage unit 24 stores six injection protocols A to F shown in the following Table 1, and the protocol generation unit 16 can read out one corresponding to information on the imaging site and information on the imaging subject (for example, injection protocol A) from these injection protocols.

TABLE 1

| Imaging site | Body weight (kg) | First phase Injection rate (mL/sec) Start | End | Injection volume (mL) | Second phase Injection rate (mL/sec) Start | End | Injection volume (mL) |
|---|---|---|---|---|---|---|---|
| A Aorta | 40 | 5.2 | 2.5 | 28 | 2.6 | 2.4 | 20 |
| B Aorta | 45 | 5.2 | 2.7 | 30 | 2.8 | 2.4 | 20 |
| C Aorta | 50 | 5.2 | 3.3 | 33 | 3.4 | 3.2 | 20 |
| D Aorta | 55 | 5.3 | 3.5 | 35 | 3.6 | 3.4 | 25 |
| E Aorta | 60 | 4.3 | 3.3 | 30 | 3.5 | 3.2 | 25 |
| F Aorta | 65 | 4.3 | 3.3 | 30 | 3.6 | 3.3 | 25 |

When the protocol generation unit 16 generates the injection protocol, the display control unit 15 causes the touch panel 26 as a display unit to display the injection protocol received from the protocol generation unit 16 (S16). Then, the operator confirms the displayed injection protocol and when the operator does not regenerate the injection protocol (NO in S17), the generation of the injection protocol ends.

Thereafter, the operator presses a check button displayed on the touch panel 26 or the final confirmation button of the injection head 21. As a result, preparation for injection is completed, and the injection apparatus 2 stands by in the injectable state.

In the case of regenerating the injection protocol (YES in S17), the operator inputs at least one of the expected pixel value of the imaging site and the expected duration of the expected pixel value via the touch panel 26 as the input unit. Then, the imaging condition acquiring unit 14 acquires at least one of the expected pixel value and the expected duration as the imaging condition via the touch panel 26 as the input unit (S18). Then, the protocol generation unit 16 regenerates the injection protocol based on the expected pixel value or the expected duration (S19).

To be specific, the storage unit 24 stores a plurality of injection protocols for achieving at least one of an expected pixel value and expected duration for each of the information on the imaging site and the information on the imaging subject. Then, the protocol generation unit 16 regenerates the injection protocol by reading the injection protocol that achieves the expected pixel value or the expected duration that has been input, from among these protocols. This completes regeneration of the injection protocol. Then, the display control unit 15 displays, on the touch panel 26, the injection rate and the injection volume included in the injection protocol received from the protocol generation unit 16.

Example 1

Figure 4:
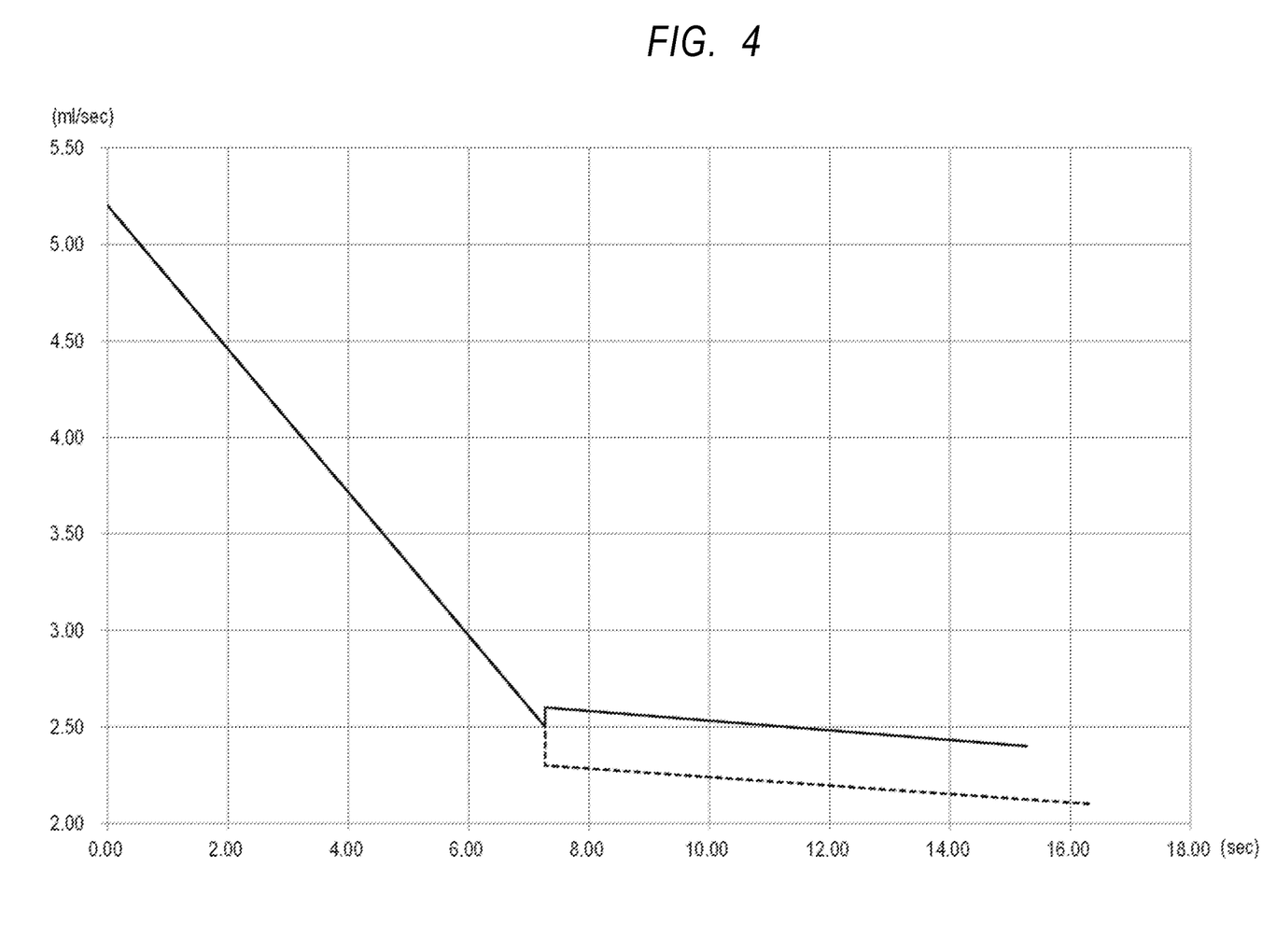
FIG. 4 is a graph showing an injection protocol.

The generated injection protocol will be described with reference to FIGS. 4 and 5. FIG. 4 is a graph showing an injection protocol according to Example 1 and Comparative Example 1. In FIG. 4, the vertical axis represents the injection rate (mL/sec) and the horizontal axis represents the elapsed time (sec) from the start of injection.

In Example 1 shown by a solid line, the change in the injection rate is shown in the case where the imaging site is an aorta and the test subject's body weight is 40 kg. Also, the iodine content of the contrast medium to be used is 300 mgI/mL, the expected pixel value is 400 HU, and the expected duration is 5 seconds. In the first phase of the example, the injection rate at the start is 5.2 mL/sec, the injection rate at the end is 2.5 mL/sec, the total injection volume is 28 mL, and the injection time is 7.27 seconds. In the second phase, the injection rate at the start is 2.6 mL/sec, the injection rate at the end is 2.4 mL/sec, the total injection volume is 20 mL, and the injection time is 8 seconds.

In the first phase of Example 1, the injection is started at an injection rate of 5.2 mL/sec. Then, the injection rate gradually decreases and when 7.27 seconds have elapsed from the start of injection, the first phase is terminated at an injection rate of 2.5 mL/sec. Subsequently, in the second phase of Example 1, the injection is started at an injection rate of 2.6 mL/sec so that the injection rate at the start is higher than the injection rate at the end of the first phase. Then, the injection rate gradually decreases and when 8 seconds have elapsed from the start of injection, the second phase is terminated at an injection rate of 2.4 mL/sec. After that, a pushing injection with physiological saline (injection rate: 2.1 mL/sec, injection volume 30 mL) is performed.

In Example 1, the protocol generation unit 16 generates an injection protocol so as to linearly decrease the injection rate in the first phase or the second phase. Further, the protocol generation unit 16 generates an injection protocol so that the second acceleration is greater than the first acceleration.

That is, the second acceleration in the second phase of Example 1 is $-0.025$ mL/s$^2$, which is greater than the first acceleration $-0.371$ mL/s$^2$ in the first phase. Furthermore, the protocol generation unit 16 generates an injection protocol so that the injection time in the second phase is longer than the injection time in the first phase. That is, the injection time in the second phase of Example 1 is 8 seconds, which is longer than the injection time 7.27 seconds in the first phase.

In addition, the protocol generation unit 16 generates an injection protocol so that the injection rate at the start of the second phase is lower than the injection rate at the start of the first phase. That is, the injection rate at the beginning of the second phase of Example 1 is 2.6 mL/sec, which is lower than the injection rate 5.2 mL/sec at the beginning of the first phase. Furthermore, the protocol generation unit 16 generates an injection protocol so that the change amount of the injection rate in the second phase is smaller than the change amount of the injection rate in the first phase. That is, the change amount of the injection rate in the second phase of Example 1 (difference between the injection rate at the start and the injection rate at the end) is 0.2 mL/sec, which is smaller than the change amount 2.7 mL/sec of the injection rate in the first phase.

In addition, the protocol generation unit 16 generates the injection protocol so that the injection volume in the second phase is smaller than the injection volume in the first phase. That is, the injection volume of the second phase of Example 1 is 20 mL, which is smaller than the injection volume 28 mL of the first phase.

Comparative Example 1

Also in the comparative example indicated by the broken line, a change in the injection rate is shown when the imaging site is an aorta and the body weight of the test subject is 40 kg. Besides, the iodine content of the contrast medium to be used is 300 mgI/mL, the expected pixel value is 400 HU, and the expected duration is 5 seconds. In the first phase of the comparative example, the injection rate at the start is 5.2 mL/sec, the injection rate at the end is 2.5 mL/sec, the total injection volume of the contrast medium is 28 mL, and the injection time is 7.27 seconds. On the other hand, in the second phase, the injection rate at the start is 2.3 mL/sec, the injection rate at the end is 2.1 mL/sec, the total injection volume is 20 mL, and the injection time is 9.09 seconds.

Also in Comparative Example 1, in the first phase, the injection is started at an injection rate of 5.2 mL/sec. Then, the injection rate gradually decreases and when 7.27 seconds have elapsed from the start of injection, the first phase ends at an injection rate of 2.5 mL/sec. However, unlike Example 1, the injection rate at the start in the second phase is lower than the injection rate at the end of the first phase. That is, in the second phase of Comparative Example 1, the injection is started at an injection rate of 2.3 mL/sec, which is lower than 2.5 mL/sec. Then, the injection rate gradually decreases and when 9.09 seconds have elapsed from the start of injection, the second phase is terminated at an injection rate of 2.1 mL/sec. Then, a pushing injection with physiological saline (injection rate: 2.1 mL/sec, injection volume 30 mL) is performed.

As shown in Example 1 of FIG. 4, the degree of reduction in the second phase of the injection protocol according to the first embodiment is gentler than that of the first phase. That is, the negative acceleration in the first phase is less than the negative acceleration in the second phase. To be specific, the acceleration in the first phase is $-0.371$ mL/s$^2$, and the acceleration in the second phase is $-0.025$ mL/s$^2$ in Example 1.

Figure 5:
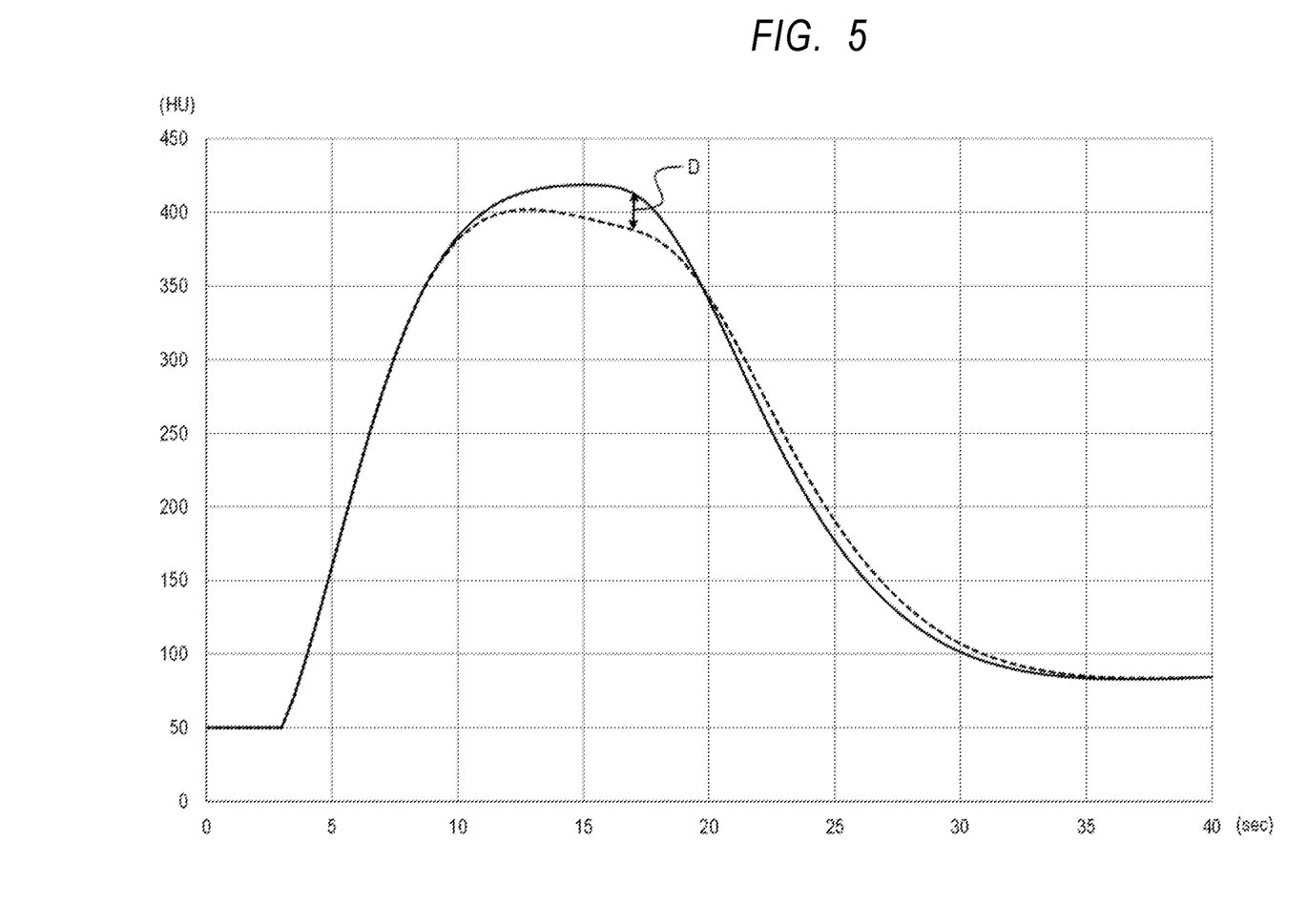
FIG. 5 is a graph showing a time density curve.

FIG. 5 is a graph showing the time density curve of each of Example 1 and Comparative Example 1. In FIG. 5, the vertical axis represents the pixel value (HU), and the horizontal axis represents the elapsed time (sec) from the start of the injection. In addition, the time density curve according to Example 1 is indicated by a solid line, and the time density curve according to Comparative Example 1 is indicated by a broken line.

In the time density curve according to Example 1, the pixel value larger than the pixel value 400 HU is maintained for 6 seconds from the point when 11.5 seconds have elapsed to the point when 17.5 seconds have elapsed from the injection start. On the other hand, in the time density curve according to Comparative Example 1, the pixel value is maintained to be larger than the pixel value 400 HU for 1.5 seconds from the point when 12 seconds have elapsed to the point when 13.5 seconds have elapsed from the injection start. However, the pixel value has decreased to about 388 HU at the point when 5 seconds, which is the expected duration, have elapsed after the point when 12 seconds have elapsed and the pixel value exceeds 400 HU, that is, when 17 seconds have elapsed. During this 5 seconds, the maximum pixel value is about 402 HU and the minimum pixel value is about 388 HU. Therefore, the fluctuation range of the pixel value is 14 HU. Also, at the point when 17 seconds have elapsed, the pixel value is about 413 HU in Example 1, so the pixel value difference D (FIG. 5) between Example 1 and Comparative Example 1 is 24 HU.

In Comparative Example 1, the pixel value fluctuates in the latter half of the expected duration and falls to a value less than the expected pixel value. On the other hand, the pixel value is maintained to be equal to or larger than the expected pixel value even in the latter half of the expected duration according to Example 1. That is, the pixel value is maintained to be larger than the expected pixel value for about 6 seconds, which exceeds the expected duration 5 seconds. Further, during a period of 5 seconds from the point when 12 seconds have elapsed to the point when 17 seconds have elapsed, the maximum pixel value is about 419 HU and the minimum pixel value is about 410 HU. Therefore, the fluctuation range of the pixel value is suppressed to 9 HU. The total injection volume of the contrast medium in Example 1 is 48 mL which is the same as in Comparative Example 1.

According to the injection protocol generated on the basis of the first embodiment described above, the pixel value can be maintained in a state where fluctuation of the pixel value is small over expected duration at the time of imaging of the imaging subject. Furthermore, since fluctuation in the pixel value can be suppressed without increasing the injection volume of the contrast medium, fluctuation in the pixel, value can be suppressed without increasing a burden on the imaging subject. Also, by entering an expected pixel value or expected duration, an injection protocol can be generated that achieves the pixel value or duration within a range desired by the operator.

It should be noted that the protocol generation unit 16 may read the injection protocol corresponding to the expected pixel value from the storage unit 24 first and then regenerate the injection protocol based on information on the imaging site and information on the imaging subject. Also, injection protocols that linearly reduce the injection rate include an injection protocol that decreases the rate linearly and an injection protocol that decreases the rate curvilinearly. Also, the number of phases is not limited to two, and may be three or more.

Further, when generating the injection protocol, the same value may be used as the usage amount per body weight in the first phase and the second phase. Furthermore, the injection rate at the beginning of the second phase may be the same as the injection rate at the beginning of the first phase. In addition, the second acceleration of the second phase may be equal to or less than the first acceleration of the first phase. Also, the injection time in the second phase can also be made shorter than the injection time in the first phase.

Second Embodiment

Subsequently, the second embodiment will be described with reference to FIG. 6. In the first embodiment, the injection apparatus 2 is provided with a generation device of the injection protocol, but in the second embodiment, the imaging apparatus 3 includes the generation device. Incidentally in the description of the second embodiment, differences from the first embodiment will be described, and the same reference numerals are given to the components described in the first embodiment, and description thereof will be omitted. Unless otherwise described, the components denoted by the same reference numerals have substantially the same operation and function, and the action and effect thereof are also substantially the same.

Figure 6:
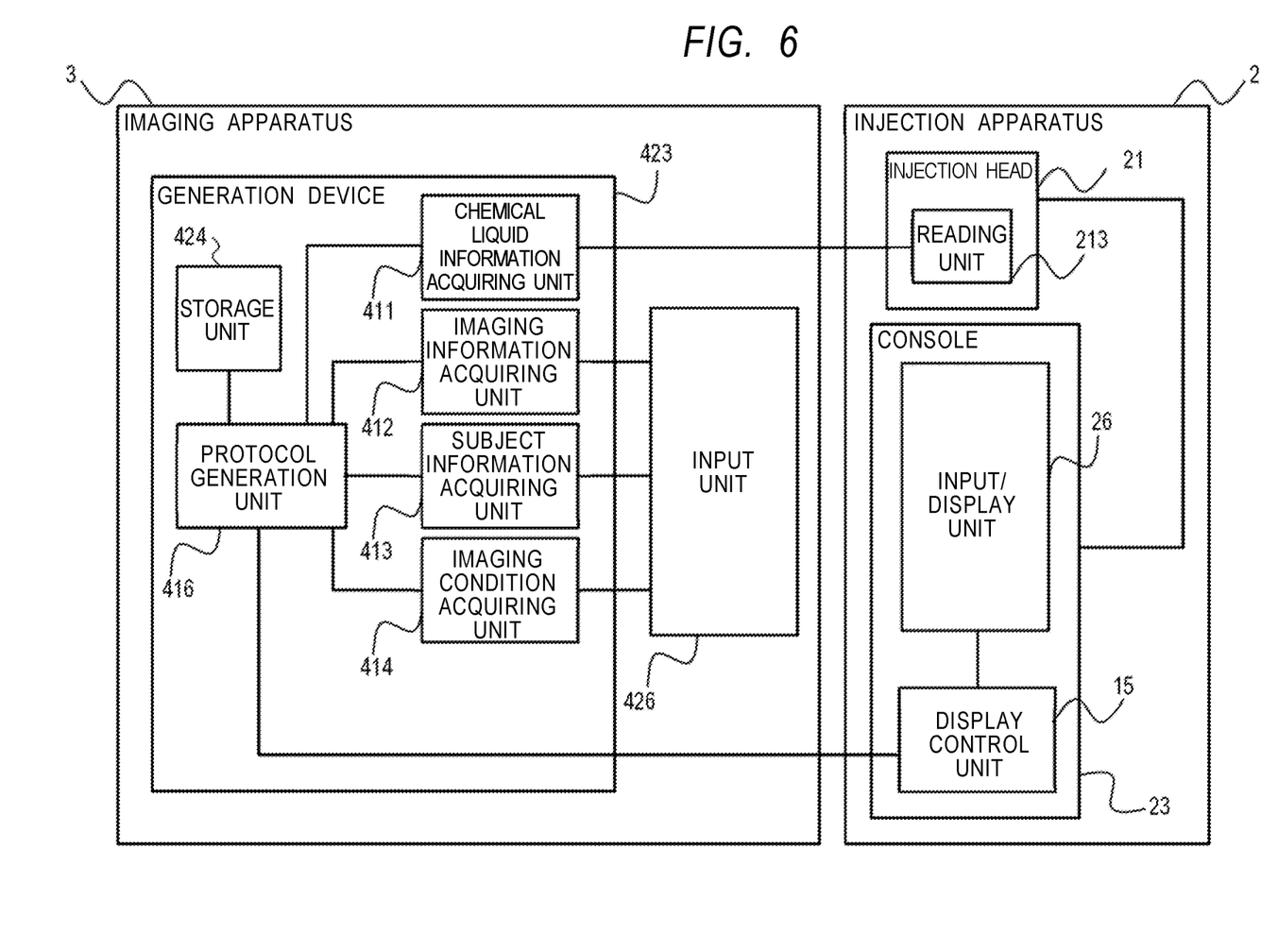
FIG. 6 is a schematic block diagram of an imaging system according to a second embodiment of the present invention.

FIG. 6 is a schematic block diagram of an imaging system including the imaging apparatus 3 and the injection apparatus 2. As shown in FIG. 6, the injection apparatus 2 includes the injection head 21 for injecting a chemical liquid and the console 23. The console 23 has the touch panel 26 as an input/display unit and the display control unit 15 for controlling the touch panel 26 as a display unit.

The imaging apparatus 3 includes a generation device 423 for an injection protocol (for example, a CPU). The generation device 423 includes a chemical liquid information acquiring unit 411 for acquiring chemical liquid information, an imaging information acquiring unit 412 for acquiring information on the imaging site of an imaging subject, a subject information acquiring unit 413 that acquires information on the imaging subject, an imaging condition acquiring unit 414 that acquires at least one of an expected, pixel value and expected duration, and a protocol generation, unit 416 for generating an injection protocol based on the information on the imaging site and the information on the imaging subject. Then, the injection apparatus 2 receives the injection protocol generated by the generation device 423 from the imaging apparatus 3, and injects the contrast medium according to the received injection protocol.

The generation device 423 executes various processing corresponding to a program installed in a storage unit 424, whereby each unit is logically operated as various functions. The storage unit 424 has a RAM as a system work memory for operating the generation device 423, a ROM for storing a program, system software or the like, or a hard disk drive, etc. Alternatively, the generation device 423 can execute various processing according to a program stored in a portable recording medium such as a CD and a DVD, or an external storage medium such as a server on the Internet.

To be more specific, when the operator mounts a syringe on the injection head 21 after turning on the power supply of the injection apparatus 2, the reading unit 213 of the injection head 21 reads chemical liquid information and sends the information to the chemical liquid information acquiring unit 411. Then, the chemical liquid information acquiring unit 411 acquires the chemical liquid information from the reading unit 213. The protocol generation unit 416 causes the storage unit 424 to store temporarily the chemical liquid information acquired by the chemical liquid information acquiring unit 411.

The imaging apparatus 3 has a user interface such as a keyboard and a touch panel as an input unit 426. Then, the operator inputs the imaging site via the input unit 426. Then, the imaging information acquiring unit 412 acquires the name of the imaging site as the imaging information from the input unit 426. Then, the protocol generation unit 416 causes the storage unit 424 to store temporarily the imaging information acquired by the imaging information acquiring unit 412. Alternatively, the imaging information acquiring unit 412 can acquire imaging information stored in the storage unit 424 in advance from the unit.

Subsequently, the operator inputs the subject information via the input unit 426. Then, the subject information acquiring unit 413 acquires the subject information via the input unit 426. Thereafter, the protocol generation unit 416 causes the storage unit 424 to store temporarily the subject information acquired by the subject information acquiring unit 413. Alternatively, the subject information acquiring unit 413 can acquire subject information stored in the storage unit 424 in advance from the unit.

The protocol generation unit 416 generates the injection protocol of the contrast medium by calculation as in the first embodiment based on information on the imaging site and information on the imaging subject. Alternatively, the protocol generation unit 416 may read the injection protocol corresponding to the information on the imaging site and the information on the imaging subject from the storage unit 424, thereby generating the injection protocol.

When the injection protocol is generated, the display control unit 15 of the injection apparatus 2 receives the injection protocol from the protocol generation unit 416 and causes the touch panel 26 as a display unit to display the protocol. Then, the operator confirms the displayed injection protocol, and when it is not necessary to change the injection protocol, generation of the injection protocol is terminated. Thereafter, the operator presses the check button displayed on the touch panel 26 or the final confirmation button of the injection head 21. As a result, preparation for injection is completed, and the injection apparatus 2 stands by in the injectable state.

The storage unit 424 stores a plurality of injection protocols for achieving at least an expected pixel value or expected duration for each of the information on the imaging site and the information on the imaging subject. The protocol generation unit 416 can regenerate the injection protocol by reading out an injection protocol that achieves the expected pixel value or the expected duration from among these protocols. In this case, the imaging condition acquiring unit 414 acquires information on at least one of the expected pixel value and the expected duration as the imaging condition via the input unit 426.

Even by the injection protocol generated based on the second embodiment described above, when an image of an imaging subject is captured, the pixel value can be maintained in a state in which fluctuation of the pixel value is small over expected duration. Furthermore, since fluctuations in a pixel value can be suppressed without increasing the injection volume of the contrast medium, fluctuations in the pixel value can be suppressed without increasing a burden on the imaging subject. Also, an injection protocol can be generated that achieves a pixel value or duration within a range desired by the operator with input of an expected pixel value or expected duration.

When the imaging apparatus 3 of the second embodiment includes the display 33, the display 33 may display the injection protocol or the like in addition to or instead of the touch panel 26 of the injection apparatus 2. Further, the operator can input imaging information, subject information and imaging conditions (expected pixel value or expected duration) from the touch panel 26 in place of the input unit 426.

Although the present invention has been described with reference to the respective embodiments, the present invention is not limited to the above-described embodiments. Invention which has been modified within the range not in violation of the present invention and invention equivalent to the present invention are also included in the present invention. In addition, each embodiment and each modification example can be appropriately combined within a scope not in violation of the present invention.

For example, the injection protocol generation device can be configured separately from the imaging apparatus 3 and the injection apparatus 2. In this case, the generation device is connected to the injection apparatus 2 in a wired or wireless manner and the injection apparatus 2 receives the injection protocol generated by an external generation device. Then, the injection apparatus 2 injects a contrast medium according to the received injection protocol. Further, the present invention is not limited to generation of an injection protocol which maintains a pixel value exceeding an expected pixel value. For example, an injection protocol may be generated which maintains a pixel value within a predetermined range from the expected pixel value.

Also, the protocol generation unit can correct the generated injection protocol based on the correction information received by the generation device. The correction information includes information on the amount of iodine per body weight for each imaging site, a heart rate and stroke volume of the imaging subject, a manufacturer name of the imaging apparatus, an imaging method, a tube voltage and the number of rows, etc. The operator can input this correction information via the touch panel 26. Furthermore, the generation device can acquire the correction information from an external server or the imaging apparatus 3.

For example, when the operator inputs a stroke volume of the imaging subject as correction information, the generation device receives the stroke volume via the touch panel 26 as the input unit. Then, when the stroke volume is equal to or larger than a predetermined amount, the protocol generation unit corrects the generated injection protocol so as to increase the injection rate or the injection time in order to increase the injection volume of the contrast medium. Conversely, when the stroke volume is less than a predetermined amount, the protocol generation unit corrects the generated injection protocol so as to decrease the injection rate or the injection time in order to reduce the injection volume of the contrast medium.

Further, the injection apparatus 2 or the imaging system 100 can transmit information on the injection result (injection history) to an external storage device such as an RIS via a network to store the information therein.

This application claims priority from Japanese Patent Application No. 2016-224084 filed on Nov. 17, 2016, the entire contents of which are incorporated herein by reference.

What is claimed is:

1. An injection apparatus generating an injection protocol including a first phase and a second phase to increase an injection volume at a start of the second phase for suppressing decrease in a pixel value of an imaging site of an imaging subject in a latter half of an expected duration, the injection apparatus comprising:
a console having a CPU, wherein the CPU is configured to:
acquire information of the imaging site of the imaging subject;
read usage volume per body weight, which is associated with the information of the imaging site;
read information of the imaging subject, which includes at least body weight of the imaging subject; and
generate, based on the information of the imaging site and the information of the imaging subject, the injection protocol including the first phase in which an injection rate linearly decreases with a first acceleration, and the second phase which serially follows the first phase and in which the injection rate linearly decreases with a second acceleration, and calculate the injection rate at the start of the second phase, which is higher than the injection rate at an end of the first phase, by using the usage volume per body weight and the body weight, and
an injection head controlled by the console to inject a contrast medium according to the generated injection protocol.

2. The injection apparatus according to claim 1, wherein the CPU is further configured to generate the injection protocol so that an absolute value of the second acceleration is smaller than an absolute value of the first acceleration.

3. The injection apparatus according to claim 1, wherein the CPU is further configured to generate the injection protocol so that injection time in the second phase is longer than injection time in the first phase.

4. The injection apparatus according to claim 1, wherein the CPU is further configured to generate the injection protocol so that the injection rate at the start of the second phase is lower than the injection rate at a start of the first phase.

5. The injection apparatus according to claim 1, wherein the CPU is further configured to generate the injection protocol so that a change amount of the injection rate in the second phase is smaller than a change amount of the injection rate in the first phase.

6. The injection apparatus according to claim 1, wherein the CPU is further configured to generate the injection protocol so that an injection volume in the second phase is smaller than an injection volume in the first phase.

7. The injection apparatus according to claim 1, wherein the CPU is further configured to acquire a name of the imaging site as the information of the imaging site.

8. The injection apparatus according to claim 1, wherein the CPU is further configured to acquire information of at least one of an expected pixel value and expected duration, wherein the CPU is further configured to generate the injection protocol so as to achieve the expected pixel value or the expected duration.

9. A control method of an injection apparatus which generates an injection protocol including a first phase and a second phase to increase an injection volume at a start of the second phase for suppressing decrease in a pixel value of an imaging site of an imaging subject in a latter half of an expected duration, the control method comprising:
acquiring information of the imaging site of the imaging subject;

reading usage volume per body weight, which is associated with the information of the imaging site;
reading information of the imaging subject, which includes at least body weight of the imaging subject;
generating, based on the information of the imaging site and the information of the imaging subject, the injection protocol including the first phase in which an injection rate linearly decreases with a first acceleration and the second phase which serially follows the first phase and in which the injection rate linearly decreases with a second acceleration,
calculating the injection rate at a start of the second phase, which is higher than the injection rate at an end of the first phase, by using the usage volume per body weight and the body weight; and
controlling an injection head of the injection apparatus to inject a contrast medium according to the generated injection protocol.

\* \* \* \* \*